United States Patent
Moody et al.

(10) Patent No.: US 11,850,072 B2
(45) Date of Patent: Dec. 26, 2023

(54) REDUCTION OF PRESSURE FROM SURFACE MOUNT COMPONENTS IN A MEDICAL SENSOR

(71) Applicant: Covidien LP, Mansfield, MA (US)

(72) Inventors: Derek L. Moody, Longmont, CO (US); Linden A. Reustle, Milliken, CO (US); Sarah L. Hayman, Boulder, CO (US); Jacob Dove, Lafayette, CO (US); Michael Kertser, Jerusalem (IL); Shai Fleischer, Modiin (IL)

(73) Assignee: COVIDIEN LP, Mansfield, MA (US)

( * ) Notice: Subject to any disclaimer, the term of this patent is extended or adjusted under 35 U.S.C. 154(b) by 47 days.

(21) Appl. No.: 16/904,652

(22) Filed: Jun. 18, 2020

(65) Prior Publication Data
US 2021/0393205 A1 Dec. 23, 2021

(51) Int. Cl.
*A61B 5/00* (2006.01)
*A61B 5/1455* (2006.01)

(52) U.S. Cl.
CPC .......... *A61B 5/6843* (2013.01); *A61B 5/6833* (2013.01); *A61B 5/14552* (2013.01)

(58) Field of Classification Search
CPC . A61B 5/6843; A61B 5/6833; A61B 5/14552; A61B 5/6826
See application file for complete search history.

(56) References Cited

U.S. PATENT DOCUMENTS

| 5,469,845 | A | * | 11/1995 | DeLonzor | A61B 5/02427 |
| | | | | | 356/41 |
| 5,891,026 | A | * | 4/1999 | Wang | A61B 5/6833 |
| | | | | | 600/344 |
| 2008/0208023 | A1 | | 8/2008 | Gruvac et al. | |
| 2013/0060109 | A1 | | 3/2013 | Besko et al. | |
| 2013/0158372 | A1 | | 6/2013 | Haisley et al. | |
| 2014/0005557 | A1 | | 1/2014 | Rich et al. | |

OTHER PUBLICATIONS

International Application No. PCT/US2021/037727 International Search Report and Written Opinion dated Oct. 4, 2021, 11 pages.
Geerligs et al., "Skin layer mechanics", Materials Science, Jan. 1, 2010, 123 pp.
Geerligs, "A literature review of the mechanical behavior of the stratum corneum, the living epidermis and the subcutaneous fat tissue", Philips Research, Jun. 30, 2006, 39 pp.
Van Kuilenburg et al., "Contact modeling of human skin: What value to use for the modulus of elasticity?", Proc IMecE: Part J: J Engineering Tribology, vol. 227, No. 4, Nov. 7, 2012, pp. 349-361.

* cited by examiner

*Primary Examiner* — Kaylee R Wilson
*Assistant Examiner* — Abid A Mustansir
(74) *Attorney, Agent, or Firm* — Fletcher Yoder, P.C.

(57) ABSTRACT

A patient monitoring sensor having a communication interface, through which the patient monitoring sensor can communicate with a monitor is provided. The patient monitoring sensor includes a light-emitting diode (LED) communicatively coupled to the communication interface and a detector, communicatively coupled to the communication interface, capable of detecting light. The patient monitoring sensor includes a layer of material is provided over protruding components on the patient-side of the sensor to reduce the contact pressure of such protruding components.

16 Claims, 5 Drawing Sheets

REDUCTION OF PRESSURE FROM SURFACE MOUNT COMPONENTS IN A MEDICAL SENSOR

FIELD

The present disclosure relates generally to medical devices, and more particularly, to medical devices that monitor physiological parameters of a patient, such as pulse oximeters.

BACKGROUND

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient uses attenuation of light to determine physiological characteristics of a patient. This is used in pulse oximetry, and the devices built based upon pulse oximetry techniques. Light attenuation is also used for regional or cerebral oximetry. Oximetry may be used to measure various blood characteristics, such as the oxygen saturation of hemoglobin in blood or tissue, the volume of individual blood pulsations supplying the tissue, and/or the rate of blood pulsations corresponding to each heartbeat of a patient. The signals can lead to further physiological measurements, such as respiration rate, glucose levels or blood pressure.

One issue in such sensors relates to pressure that a sensor may place on a patient's skin. Any protruding part in the sensor package can deflect a portion of the patient's skin, causing discomfort, tissue necrosis, or other issues related to prolonged deflection of or excessive pressure on patient skin surface. While mechanical skin models vary considerably dependent upon body site, age, gender, hydration of the skin, etc., the present disclosure recognizes that there is a need in the art for medical sensors that avoid such concerns.

SUMMARY

The techniques of this disclosure generally relate to medical devices that monitor physiological parameters of a patient, such as pulse oximeters.

In one aspect, the present disclosure provides a patient monitoring sensor having a communication interface, through which the patient monitoring sensor can communicate with a monitor. The patient monitoring sensor also includes a light-emitting source, for example a light-emitting diode (LED), communicatively coupled to the communication interface and a detector, communicatively coupled to the communication interface, capable of detecting light. In exemplary embodiments, a layer of material is provided over protruding components on the patient-side of the sensor to reduce the contact pressure of such protruding components. In further exemplary embodiments, such protruding parts comprise one or more of a light source, detector, and flex circuit housing.

In another aspect, the disclosure provides a patient monitoring sensor having a communication interface, through which the patient monitoring sensor can communicate with a monitor, wherein the sensor also includes a surface mount LED with an at least partially transparent disc or a ring positioned over at least a portion of the surface mount LED on the patent-side of the sensor.

In another aspect, the disclosure provides a patient monitoring sensor having a communication interface, through which the patient monitoring sensor can communicate with a monitor, wherein the sensor also includes a detector with an at least partially transparent disc or a ring positioned over at least a portion of the detector on the patent-side of the sensor.

In another aspect, the disclosure provides a patient monitoring system, having a patient monitor coupled to a patient monitoring sensor. The patient monitoring sensor includes a communication interface, through which the patient monitoring sensor can communicate with the patient monitor. The patient monitoring sensor also includes a light-emitting diode (LED) communicatively coupled to the communication interface and a detector, communicatively coupled to the communication interface, capable of detecting light. The patient monitoring sensor further includes a layer of material provided over protruding components on the patient-side of the sensor to reduce the contact pressure of such protruding components.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Traditional pulse oximeter sensor designs utilize leadframe package LEDs that provide somewhat smooth profiles compatible with surrounding bandage materials. While such traditional pulse oximeter sensor designs can include protrusions that induce localized contact pressure on patient skin, other designs can provide much greater contact pressure problems.

For example, surface mount LEDs, which provide benefit by virtue of open high-power options, and photodetectors can provide smaller overall packaging (including length, width and height) and can reduce the profile of a sensor for a flatter sensor; however such components can be so narrow (length and width) that they can create higher pressure on a patient's skin due to the smaller contact area. This higher pressure can cause discomfort, tissue necrosis or other problems.

Accordingly, the present disclosure describes a patient monitoring sensor that includes a material over protruding components on the patient-side of the sensor. In exemplary embodiments, the covering material increases the contact area while allowing light transmission therethrough for a light emitting device, such as an LED or detector. In one exemplary aspect, the covering material is a flap with an aperture therethrough. In another exemplary aspect, the covering material comprises a disc that is at least partially transparent to light. In another exemplary aspect, the covering material is a ring with an aperture therethrough.

In another aspect, the disclosure provides a patient monitoring system, having a patient monitor coupled to a patient monitoring sensor. The patient monitoring sensor includes a communication interface, through which the patient monitoring sensor can communicate with the patient monitor. The patient monitoring sensor also includes a light-emitting diode (LED) communicatively coupled to the communication interface and a detector capable of detecting light. The patient monitoring sensor includes a material over protruding components on the patient-side of the sensor.

Figure 1:
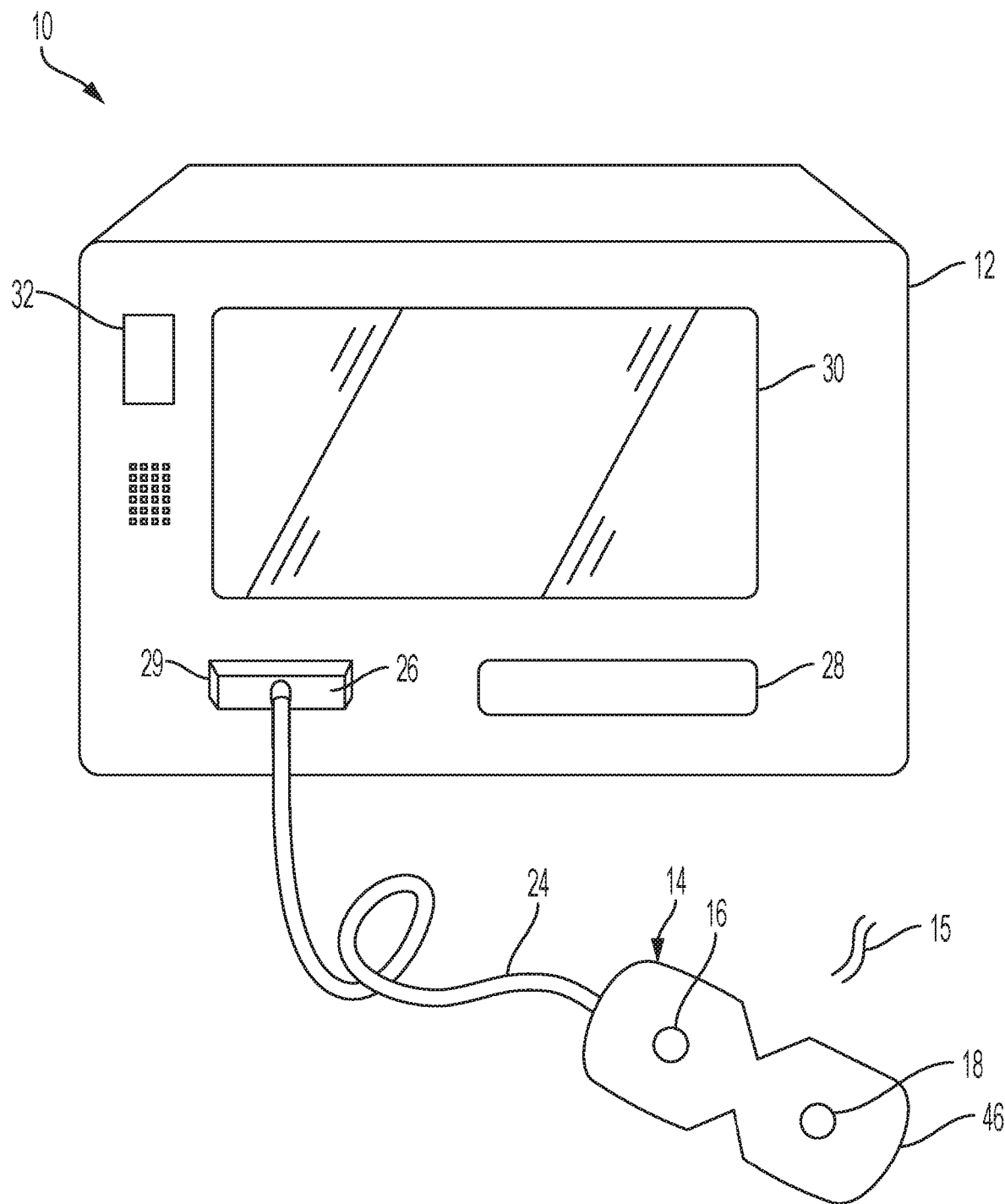
FIG. 1 illustrates a perspective view of an exemplary patient monitoring system including a patient monitor and a patient monitoring sensor, in accordance with an embodiment.

Referring now to FIG. 1, an embodiment of a patient monitoring system 10 that includes a patient monitor 12 and a sensor 14, such as a pulse oximetry sensor, to monitor physiological parameters of a patient is shown. By way of example, the sensor 14 may be a NELLCOR™, or INVOS™ sensor available from Medtronic (Boulder, Colo.), or another type of oximetry sensor. Although the depicted embodiments relate to sensors for use on a patient's fingertip, toe, or earlobe, it should be understood that, in certain embodiments, the features of the sensor 14 as provided herein may be incorporated into sensors for use on other tissue locations, such as the forehead and/or temple, the heel, stomach, chest, back, or any other appropriate measurement site.

In the embodiment of FIG. 1, the sensor 14 is a pulse oximetry sensor that includes one or more emitters 16 and one or more detectors 18. For pulse oximetry applications, the emitter 16 transmits at least two wavelengths of light (e.g., red and/or infrared (IR)) into a tissue of the patient. For other applications, the emitter 16 may transmit 3, 4, or 5 or more wavelengths of light into the tissue of a patient. The detector 18 is a photodetector selected to receive light in the range of wavelengths emitted from the emitter 16, after the light has passed through the tissue. Additionally, the emitter 16 and the detector 18 may operate in various modes (e.g., reflectance or transmission). In certain embodiments, the sensor 14 includes sensing components in addition to, or instead of, the emitter 16 and the detector 18. For example, in one embodiment, the sensor 14 may include one or more actively powered electrodes (e.g., four electrodes) to obtain an electroencephalography signal.

The sensor 14 also includes a sensor body 46 to house or carry the components of the sensor 14. The body 46 includes a backing, or liner, provided around the emitter 16 and the detector 18, as well as an adhesive layer (not shown) on the patient side. The sensor 14 may be reusable (such as a durable plastic clip sensor), disposable (such as an adhesive sensor including a bandage/liner at least partially made from hydrophobic materials), or partially reusable and partially disposable.

In the embodiment shown, the sensor 14 is communicatively coupled to the patient monitor 12. In certain embodiments, the sensor 14 may include a wireless module configured to establish a wireless communication 15 with the patient monitor 12 using any suitable wireless standard. For example, the sensor 14 may include a transceiver that enables wireless signals to be transmitted to and received from an external device (e.g., the patient monitor 12, a charging device, etc.). The transceiver may establish wireless communication 15 with a transceiver of the patient monitor 12 using any suitable protocol. For example, the transceiver may be configured to transmit signals using one or more of the ZigBee standard, 802.15.4x standards WirelessHART standard, Bluetooth standard, IEEE 802.11x standards, or MiWi standard. Additionally, the transceiver may transmit a raw digitized detector signal, a processed digitized detector signal, and/or a calculated physiological parameter, as well as any data that may be stored in the sensor, such as data relating to wavelengths of the emitters 16, or data relating to input specification for the emitters 16, as discussed below. Additionally, or alternatively, the emitters 16 and detectors 18 of the sensor 14 may be coupled to the patient monitor 12 via a cable 24 through a plug 26 (e.g., a connector having one or more conductors) coupled to a sensor port 29 of the monitor. In certain embodiments, the sensor 14 is configured to operate in both a wireless mode and a wired mode. Accordingly, in certain embodiments, the cable 24 is removably attached to the sensor 14 such that the sensor 14 can be detached from the cable to increase the patient's range of motion while wearing the sensor 14.

The patient monitor 12 is configured to calculate physiological parameters of the patient relating to the physiological signal received from the sensor 14. For example, the patient monitor 12 may include a processor configured to calculate the patient's arterial blood oxygen saturation, tissue oxygen saturation, pulse rate, respiration rate, blood pressure, blood pressure characteristic measure, autoregulation status, brain activity, and/or any other suitable physiological characteristics. Additionally, the patient monitor 12 may include a monitor display 30 configured to display information regarding the physiological parameters, information about the system (e.g., instructions for disinfecting and/or charging the sensor 14), and/or alarm indications. The patient monitor 12 may include various input components 32, such as knobs, switches, keys and keypads, buttons, etc., to provide for operation and configuration of the patient monitor 12. The patient monitor 12 may also display information related to alarms, monitor settings, and/or signal quality via one or more indicator lights and/or one or more speakers or audible indicators. The patient monitor 12 may also include an upgrade slot 28, in which additional modules can be inserted so that the patient monitor 12 can measure and display additional physiological parameters.

Because the sensor 14 may be configured to operate in a wireless mode and, in certain embodiments, may not receive power from the patient monitor 12 while operating in the wireless mode, the sensor 14 may include a battery to provide power to the components of the sensor 14 (e.g., the emitter 16 and the detector 18). In certain embodiments, the battery may be a rechargeable battery such as, for example, a lithium ion, lithium polymer, nickel-metal hydride, or nickel-cadmium battery. However, any suitable power source may be utilized, such as, one or more capacitors and/or an energy harvesting power supply (e.g., a motion generated energy harvesting device, thermoelectric generated energy harvesting device, or similar devices).

As noted above, in an embodiment, the patient monitor 12 is a pulse oximetry monitor and the sensor 14 is a pulse oximetry sensor. The sensor 14 may be placed at a site on a patient with pulsatile arterial flow, typically a fingertip, toe, forehead or earlobe, or in the case of a neonate, across a foot. Additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. The patient monitoring system 10 may include sensors 14 at multiple locations. The emitter 16 emits light which passes through the blood perfused tissue, and the detector 18 photoelectrically senses the amount of light reflected or transmitted by the tissue. The patient monitoring system 10 measures the intensity of light that is received at the detector 18 as a function of time.

A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The amount of light detected or absorbed may then be used to calculate any of a number of physiological parameters, including oxygen saturation (the saturation of oxygen in pulsatile blood, SpO2), an amount of a blood constituent (e.g., oxyhemoglobin), as well as a physiological rate (e.g., pulse rate or respiration rate) and when each individual pulse or breath occurs. For SpO2, red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood, such as from empirical data that may be indexed by values of a ratio, a lookup table, and/or from curve fitting and/or other interpolative techniques.

Figure 2:
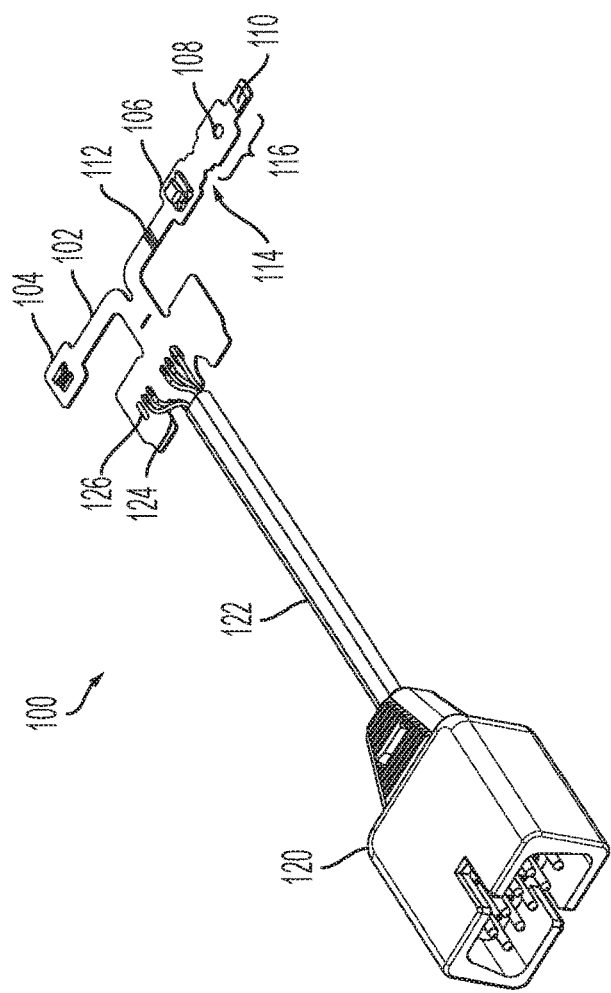
FIG. 2 illustrates a perspective view of an exemplary patient monitoring sensor, in accordance with an embodiment.

Referring now to FIG. 2, an embodiment of a patient monitoring sensor 100 in accordance with an embodiment is shown. As may be seen, the shape or profile of various components may vary. The sensor 100 includes a body 102 that includes a flexible circuit. The sensor 100 includes an LED 104 (in this case a surface mount LED) and a detector 106 disposed on the body 102 of the sensor 100.

While any number of exemplary sensor designs are contemplated herein, in the illustrated exemplary embodiment, the body 100 includes a flap portion 116 that includes an aperture 108. The flap portion 116 is configured to be folded at a hinge portion 114 such that the aperture 108 overlaps the detector 106 to allow light to pass through. In one embodiment, the flap portion 116 includes an adhesive 110 that is used to secure the flap portion 116 to the body 102 after the flap portion 116 is folded at the hinge portion 114. The exemplary flap portion 116 increases the surface area to reduce the contact pressure from the detector on the skin.

The sensor 100 includes a plug 120 that is configured to be connected to a patient monitoring system, such as the one shown in FIG. 1. The sensor 100 also includes a cable 122 that connects the plug 120 to the body 102 of the sensor 100. The cable 122 includes a plurality of wires 124 that connect various parts of the plug 120 to terminals 126 disposed on the body 102. The flexible circuit is disposed in the body 102 and connects the terminals 126 to the LED 104 and the detector 106. In addition, one of the terminals 126 connect a ground wire to the flexible circuit.

In exemplary embodiments, the aperture 108 is configured to provide electrical shielding to the detector 106. In exemplary embodiments, aperture 108 also limits the amount of light that is received by the detector 106 to prevent saturation of the detector. In exemplary embodiments, the configuration of the aperture 108, i.e., a number, shape, and size of the openings that define the aperture 108 can vary. As illustrated, in one embodiment, the aperture 108 includes a single round opening. In other embodiments, the aperture 108 can include one or more openings that have various shapes and sizes. The configuration of the aperture 108 is selected to provide electrical shielding for the detector 106 and/or control the amount of light that is received by the detector 106. In exemplary embodiments, the body 102 includes a visual indicator 112 that is used to assure proper alignment of the flap portion 116 when folded at the hinge portion 114. Further, the shape of the material of the flap portion 116 around the aperture 108 can vary, while at the same time increasing the surface area around the detector to reduce the contact pressure from the detector on the skin.

Figure 3:
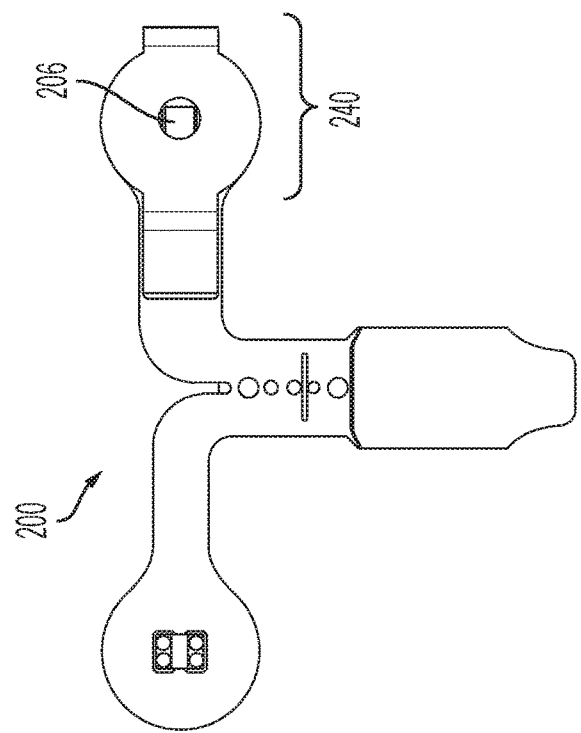
FIG. 3 illustrates a schematic view of an exemplary patient monitoring sensor, in accordance with an embodiment.

Referring now to FIG. 3, a patient monitoring sensor 200 in accordance with an embodiment is shown. In exemplary embodiments, a faraday cage 240 is formed around the detector 206 by folding the flap portion 116 over a portion of the body 102 of the sensor 200.

As we have noted, regardless of sensor configuration particulars of the above-described exemplary embodiments, at least a portion of the materials used in the construction of the sensor increases the surface area of protruding components to reduce the contact pressure from the detector on the skin. Exemplary materials include thin films made of flexible low durometer materials, e.g., plastics, foams, gels, etc. Further exemplary materials include silicone gel, thin foams, etc. that can be manufactured as thin films to reduce contact pressure of protruding components. As deflection relates to the thickness of the material along with the durometer, while lower durometer materials may be preferable, higher durometer materials could be used as very thin film layers.

As we have noted, transmission of light is desired for emitters and detectors, with emphasis on transmission of light in the red and IR ranges. The level of transparency is based on the total efficiency of the sensor; and in exemplary embodiments, the level of transparency can be selected based on the efficiency of the sensor. For example, with bright LED light and sensitive detectors (having a big active area), transparency can be lower. Options include cut holes or other apertures over areas where light transmission is desired or transparent or semi-transparent materials. One exemplary semi-transparent material includes silicone gel. Another at least partially transparent material includes polyethylene (PET). In further exemplary embodiments, use of a film as an optical filter in ranges outside of red and IR also facilitates filtering out a portion of ambient light.

In further exemplary embodiments, materials for the sensor and bandage generally comprise hydrophobic materials, for example including a polyester backing and a silicone patient adhesive.

Figure 4:
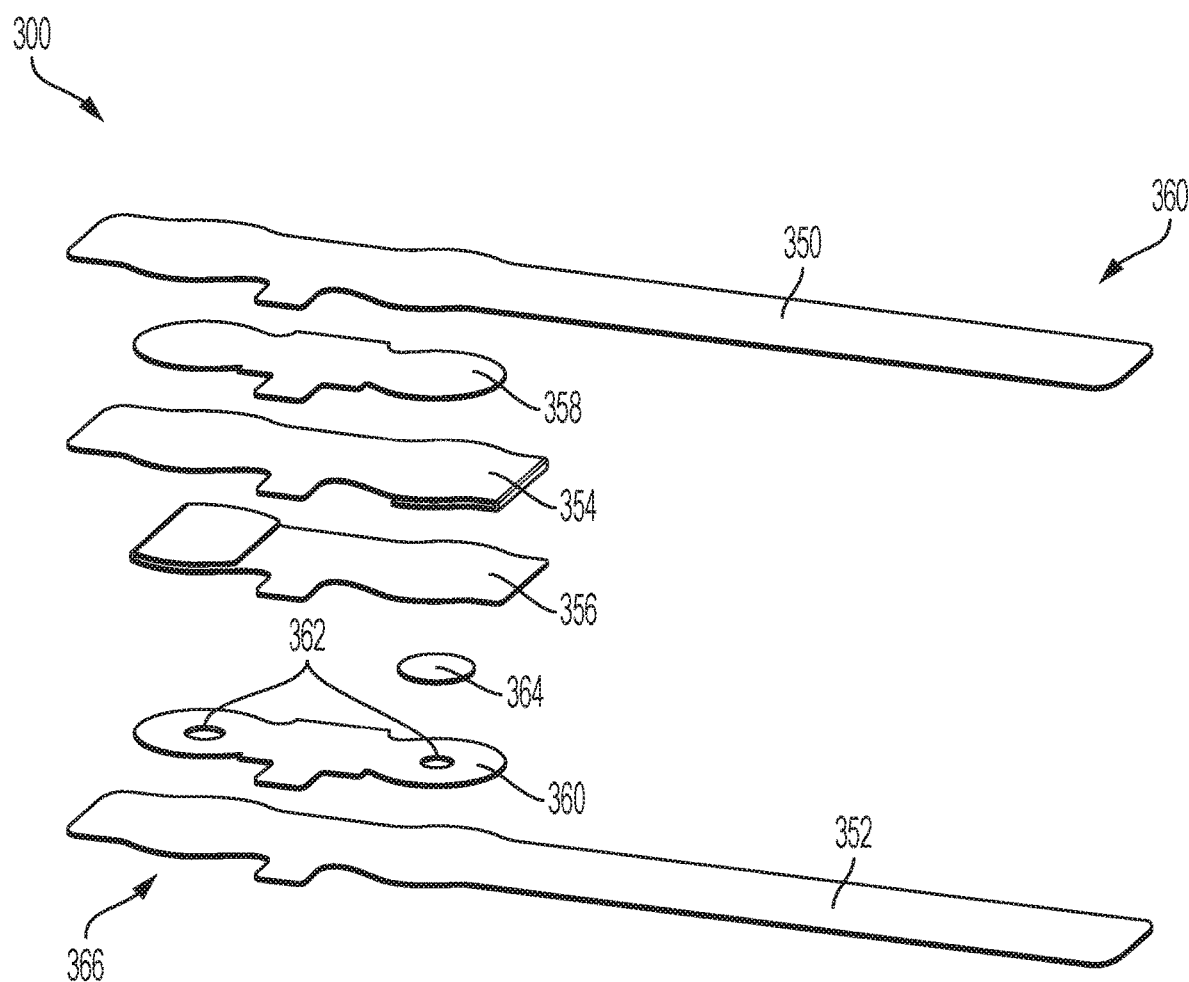
FIG. 4 illustrates a layered schematic view of an exemplary patient monitoring sensor bandage, in accordance with an embodiment.

FIG. 4 illustrates an expanded perspective view generally at 300 of an exemplary layered body/bandage configuration for a pulse oximeter sensor. The configuration includes: an upper bandage 350; an exemplary bottom tape/patient adhesive 352; exemplary top internal liner 354 and bottom internal liner 356, which in exemplary embodiments are discarded during sensor assembly, allowing the bandage to open like a leaflet to insert the flex circuit of FIGS. 2 and 3 into the bandage; a top light blocking layer 358, for example a metallized tape; a bottom light blocking layer 360, for example a metallized tape with holes 362 configured to allow light to shine through; and a disc 364, comprising for example a polyethylene material, configured to reduce pressure from the LED on the patient. In exemplary embodiments, bottom tape 352 comprises a semi-transparent adhesive layer with a release liner 366 on the patient facing side of tape 352.

Figure 5:
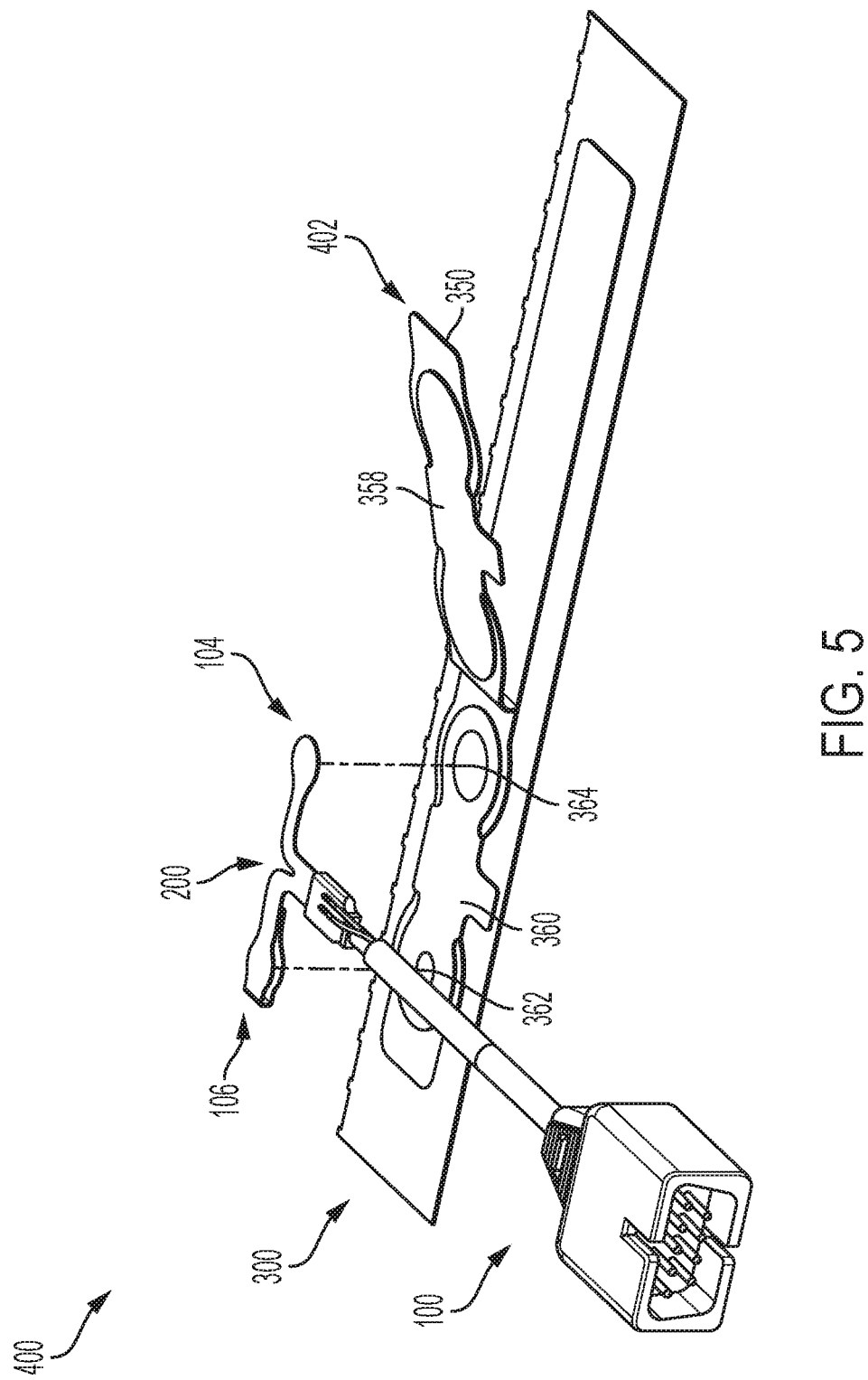
FIG. 5 illustrates a perspective view of an exemplary sensor assembly.

FIG. 5 illustrates a perspective view of exemplary assembly of the flex circuit 200 of FIGS. 2 and 3 into the bandage 300, with internal liners 354, 356 removed to allow positioning of the flex circuit 200 into the bandage, between the light blocking layers 358, 360. As is shown, detector 106 is positioned over hole 362. LED 104 is positioned over disc 364 (which is positioned over another hole 362 (not shown in FIG. 5)). Rapid assembly is facilitated by removable liners 354, 356, as well as the upper bandage 350 and light blocking layer 358 acting as a foldable leaflet 402, the exemplary bandage construction provided as a sub-assembly configured to provide high-volume, fast and repeatable production of sensor assemblies.

Exemplary materials for backing or other material includes plastics, such as polypropylene (PP), polyester (PES), polyethylene (PE), urethanes, silicone, or the like. Additionally, various layers of the device may be constructed of one or more hydrophobic materials. Bandage, backing and additional possible layers may comprise a variety of thicknesses.

In exemplary embodiments, disc 364 is a thin disc (e.g., 0.1 millimeter (mm)polyethylene, which is semi-transparent and is operative to maintain the light transmission from the LED through the PET) inserted in or integral to bandage between the LED and the patient-side of the sensor, e.g., to reduce contact pressure on the skin. Other thicknesses of materials are also contemplated, for example 0.08 mm-0.12 mm; 0.1 mm-0.15 mm, etc.

In FIGS. 4 and 5, the disc 364 is inserted between the LED and the bottom of the sensor bandage to propagate the force from the LED to a wider area. In exemplary embodiments, a PET disc 364 is converted with an acrylic adhesive on one side and die cut into an 8 millimeter (mm) disc (though ranges of sizes are contemplated, e.g., 5-12 mm, 6-10 mm, 7-9 mm, etc.) that is adhered to the bottom tape of the sensor. In exemplary embodiments, the bottom tape (352 in FIG. 4) has an adhesive facing toward the disc 364, which adheres the disc in place.

In further exemplary embodiments, the LED (104 in FIG. 2) is soldered to the flex circuit (200 in FIG. 3), which is placed on top of the adhesive side of the disc 364 (see FIG. 5). The adhesive of the disc 364 secures the disc in place relative to the LED 104.

Figure 6:
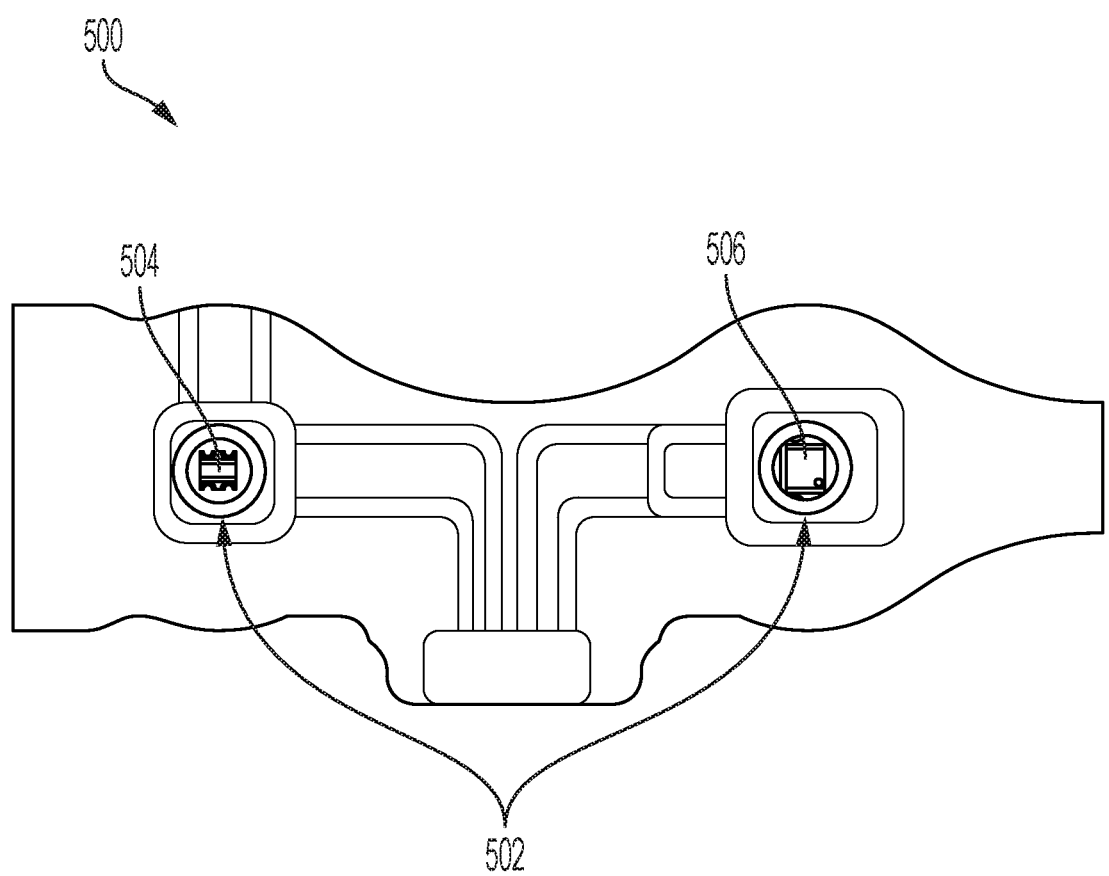
FIG. 6 illustrates a top elevation view of an exemplary sensor assembly incorporating a pressure reducing ring.

Thus, according to example embodiments described herein, the disc (or other alternative structure) reduces pressure when placed over the LED, resulting in lower perceived or felt pressure. As we have noted, while exemplary embodiments describe a disc, alternate embodiments contemplate other shapes, for example square shapes, rectangular shapes, discs, etc. FIG. 6 illustrates another exemplary sensor generally at 500, with ring materials 502 provided over LED 504 and detector 506, respectively.

One or more specific embodiments of the present techniques will be described below. In an effort to provide a concise description of these embodiments, not all features of an actual implementation are described in the specification. It should be appreciated that in the development of any such actual implementation, numerous implementation-specific decisions must be made, which may vary from one implementation to another.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A patient monitoring sensor, comprising
a communication interface, through which the patient monitoring sensor can communicate with a monitor;
a light-emitting diode (LED) communicatively coupled to the communication interface;
a detector communicatively coupled to the communication interface, wherein the detector is configured to detect light;
a light blocking layer having one or more holes configured to transmit optical signals from the LED or to the detector; and
an at least partially transparent layer of material between the light blocking layer and the LED, and not between the light blocking layer and the detector, on a patient-side of the sensor, the at least partially transparent layer of material having a thickness of from about 0.08 mm to about 1.5 mm to reduce the contact pressure of protruding portions of the LED.

2. The patient monitoring sensor of claim 1, further comprising a flap portion positioned over the detector.

3. The patient monitoring sensor of claim 1, wherein the layer of material comprises a disc or ring provided between the light blocking layer and the patient-side of the sensor.

4. The patient monitoring sensor of claim 3, wherein the layer of material comprises a disc that is at least partially transparent in a portion between the light blocking layer and the patient-side of the sensor.

5. The patient monitoring sensor of claim 3, wherein the layer of material comprises a polyethylene disc that is provided between the light blocking layer and the patient-side of the sensor.

6. The patient monitoring sensor of claim 5, wherein the polyethylene disc has a thickness of approximately one millimeter and a diameter of approximately eight millimeters.

7. The patient monitoring sensor of claim 1, further comprising an at least partially transparent disc that is provided between the light blocking layer and the patient-side of the sensor.

8. The patient monitoring sensor of claim 7, further comprising a patient-side tape adhered to a flap portion positioned over the detector and adhered to the disc provided over the LED.

9. A method for making a patient monitoring system, comprising:
coupling a light-emitting diode (LED) communicatively to a communication interface, wherein a patient monitoring sensor is configured to communicate with a monitor via the communication interface;
coupling a detector capable of detecting light communicatively to the communication interface;
positioning an at least partially transparent layer of material between a light blocking layer and the LED, and not between the light blocking layer and the detector, on a patient-side of the sensor, the light blocking layer having one or more holes configured to transmit optical signals from the LED or to the detector, and the at least partially transparent layer of material having a thickness of from about 0.08 mm to about 1.5 mm to reduce the contact pressure of protruding portions of the LED.

10. The method of claim 9, further comprising positioning a flap portion over the detector.

11. The method of claim 9, wherein the layer of material comprises a disc or ring provided between the light blocking layer and the patient-side of the sensor.

12. The method of claim 11, wherein the layer of material comprises a disc that is at least partially transparent in a portion between the light blocking layer and the patient-side of the sensor.

13. The method of claim 11, wherein the layer of material comprises a polyethylene disc that is provided between the light blocking layer and the patient-side of the sensor.

14. The method of claim 13, wherein the polyethylene disc has a thickness of approximately one millimeter and a diameter of approximately eight millimeters.

15. The method of claim 9, wherein the layer of material comprises an at least partially transparent disc that is positioned between the light blocking layer and the patient-side of the sensor.

16. The method of claim 15, further comprising adhering a patient-side tape to a flap portion that is positioned over the detector and adhered to the disc provided over the LED.

* * * * *